(12) United States Patent
Matsumura

(10) Patent No.: US 7,479,105 B2
(45) Date of Patent: Jan. 20, 2009

(54) PENILE ERECTION CONTROL METHOD AND PENILE ERECTION CONTROL DEVICE

(76) Inventor: Osamu Matsumura, 20-11, Higashi-cho, Koganei-shi, Toyko (JP)

( * ) Notice: Subject to any disclaimer, the term of this patent is extended or adjusted under 35 U.S.C. 154(b) by 306 days.

(21) Appl. No.: 11/369,813

(22) Filed: Mar. 8, 2006

(65) Prior Publication Data
US 2006/0206001 A1 Sep. 14, 2006

(30) Foreign Application Priority Data
Mar. 8, 2005 (JP) ............... 2005-063882
Jan. 24, 2006 (JP) ............... 2006-014690

(51) Int. Cl.
A61F 5/00 (2006.01)
(52) U.S. Cl. ..................................... 600/41
(58) Field of Classification Search ........... 600/38–41, 600/29–31; 606/201–203
See application file for complete search history.

(56) References Cited

U.S. PATENT DOCUMENTS 3,750,194 A * 8/1973 Summers ................. 623/23.66
4,828,544 A * 5/1989 Lane et al. ..................... 604/9
5,453,079 A * 9/1995 Schwaninger ................ 600/38

FOREIGN PATENT DOCUMENTS

JP H6-125931 5/1994
JP 2002-238933 8/2002

* cited by examiner

Primary Examiner—John P Lacyk
(74) Attorney, Agent, or Firm—Manabu Kanesaka

(57) ABSTRACT

To control the erection of a penis 10, the male sex organ, as desired, an electromagnetic valve 18 is connected to a penile vein 17 of the penis 10, the male sex organ, and ON-OFF control of this electromagnetic valve 18 is performed by a control unit 42 embedded in the body in the vicinity of the penis 10. When an external signal is supplied by a commander 54, the control unit 42 closes the electromagnetic valve 18, suppresses outflow of blood from the spongy body 21, 22, and thereby maintains the erection state of the penis 10.

14 Claims, 12 Drawing Sheets

PENILE ERECTION CONTROL METHOD AND PENILE ERECTION CONTROL DEVICE

BACKGROUND OF THE INVENTION

1. Field of the Invention

The present invention relates to an erection control method and erection control device which maintains an erection state of the penis, which is the male sex organ.

2. Description of the Related Art

Coitus is an act wherein the penis, which is the male sex organ, is inserted in the vagina, which is the female sex organ. In the vagina, the female sex organ, the surrounding tissues push outwards in contact with each other so that they are usually closed. Therefore, if the penis is not erect, it cannot be inserted in the vagina and coitus cannot be performed. Therefore, the ability of the penis to become erect is extremely important for male sexual function.

In Japanese Patent Application Laid-Open No. 6-125931, a male sexual function enhancing device is disclosed comprising a base part formed of a firm and strong material which support from the root of the male sex organ to the anus, an airbag free to expand attached to the base part on the male sex organ side, a pump which pumps air into the airbag or expels it therefrom, and a fixture attached to the body so as to support the base part from the root of the male sex organ to the anus.

This function enhancing device constricts the posterior root of the male sex organ, and constricts the vein through which blood returns to the heart from the male sex organ. Consequently, blood sent into the penis from the arteries cannot leave, and fills the spongy body of the penis causing the penis to become erect. However in practice, the airbag does not constrict the vein efficiently and reliably. Moreover, if the vein does become constricted, it interferes with the erection and actually has the reverse effect.

OBJECTS AND SUMMARY OF THE INVENTION

It is therefore an object of the present invention to provide a penile erection control method and control device which can reliably maintain the erection state of the penis.

It is a further object of the invention to provide a penile erection control method and control device which cause the penis to become erect and maintain the erection as desired.

It is a still further object of the invention to provide a penile erection control method and control device which permit the erection state of the penis to be terminated as desired.

It is a still further object of the invention to provide a penile erection control method and control device which permit the erection start time and end time to be controlled as desired.

It is a still further object of the invention to provide a penile erection control method and control device which avoid release or interruption of the erection during coitus.

It is a still further object of the invention to provide a penile erection control method and control device which permit the maintenance time of penile erection during coitus to be controlled as desired.

It is a still further object of the invention to provide a penile erection control method and control device which resolve the problem of impotence or ED (Erectile Dysfunction) by a physical technique.

The aforesaid problems and associated problems addressed by the present invention will be clarified by the technical concepts of the invention and their implementation.

One aspect of the invention relates to a penile erection control method wherein an valve means is connected to a vein which returns blood from the spongy body of the penis to the lungs, and ON-OFF control or opening adjustment of this valve means is performed by a control means. Here, the valve means may be an electromagnetic valve. Alternatively, the valve means may be an electromagnetic squeeze valve. The blood vessel to which the valve means is connected may be a penile dorsal vein. Further, the valve means may have a resilient tube and a depressor which pushes the tube, resulting in the close or squeeze of the tube when depressor acts. The resilient tube may be made of synthetic polymer and both ends thereof may be connected to the penile dorsal vein through respective connecting tubes.

Another aspect of the invention relates to a penile erection control device comprising:

a valve means connected to a vein which returns blood from the spongy body of the penis to the lungs; and a control means which performs ON-OFF control or opening adjustment of the valve means, wherein the erection state is maintained by using the control means to close or throttle the valve means.

Here, the valve means may be an electromagnetic valve. Alternatively, the valve means may be an electromagnetic squeeze valve. The valve means may be connected to a penile dorsal vein. The valve means may comprise a flexible tube and a depressor which compresses the tube, the tube being squeezed by the depressor so as to close or throttle it. The flexible tube may be made of a synthetic polymer material, and both ends may be connected to the penile dorsal vein via connecting tubes.

The control means may comprise a control unit implanted in the body which controls the opening/closing or throttling amount of the valve means, and a commander which sends control signals to the control unit. Alternatively, the control means may comprise a control unit implanted in the body which controls the opening/closing or throttling amount of the valve means, and a pressure-sensitive control panel on the outer surface of the casing of the control unit, a control signal being supplied to the control unit by pressing the control panel through the skin. Alternatively, the control means may comprise a measurement means which measures time, and when the measurement means measures a predetermined time from when the valve means is closed or throttled, it opens the valve means.

An aspect of the invention comprises an valve means connected to a vein which returns blood from the spongy body of the penis to the lungs, and a control means which performs ON-OFF control or opening adjustment of the valve means. The valve means is closed by the control means which shuts off blood leaving the spongy body of the penis, and thereby maintains a penile erection.

According to this construction, blood flowing into the veins from the penis is completely or partially shut off by closing or throttling the valve means through the control means, therefore the erection state of the penis is maintained. This erection state continues until the valve means is released, so the erection state can be controlled as desired. The above and other objects, features and advantages of this invention will be apparent from the following description of illustrative embodiments, which are to be read in connection with accompanying drawings.

DESCRIPTION OF THE PREFERRED EMBODIMENTS

Figure 1:
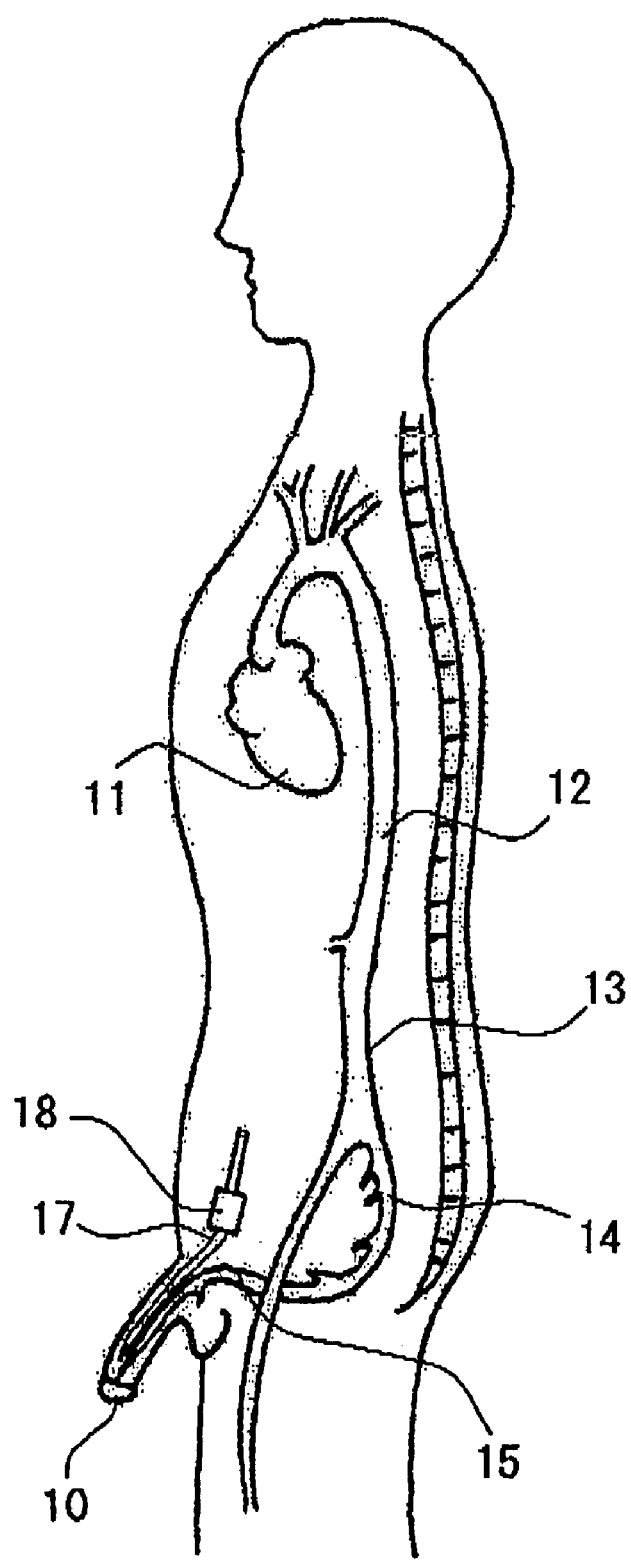
FIG. 1 is a cross-sectional side elevation of the human body showing the flow of blood from the heart to the penis.

The invention will now be described in greater detail referring to the diagrams. FIG. 1 is a schematic view of the penile erection control method and control device according to a first embodiment of the invention showing the construction of the blood vessels in the human body. The diagram shows the flow of blood from the heart 11 to the penis 10, the male sex organ, via the abdominal aorta 12, common iliac artery 13, internal iliac artery 14 and penile arteries 15 in the order 12, 13, 14, 15. The blood from the penis 10 leaves via the penile vein 17, and the blood flow due to this vein 17 is returned first to the lungs where carbon dioxide/oxygen exchange is performed, and then the heart 11. Here, an electromagnetic valve 18 is connected to the penile vein 17.

Figure 2:
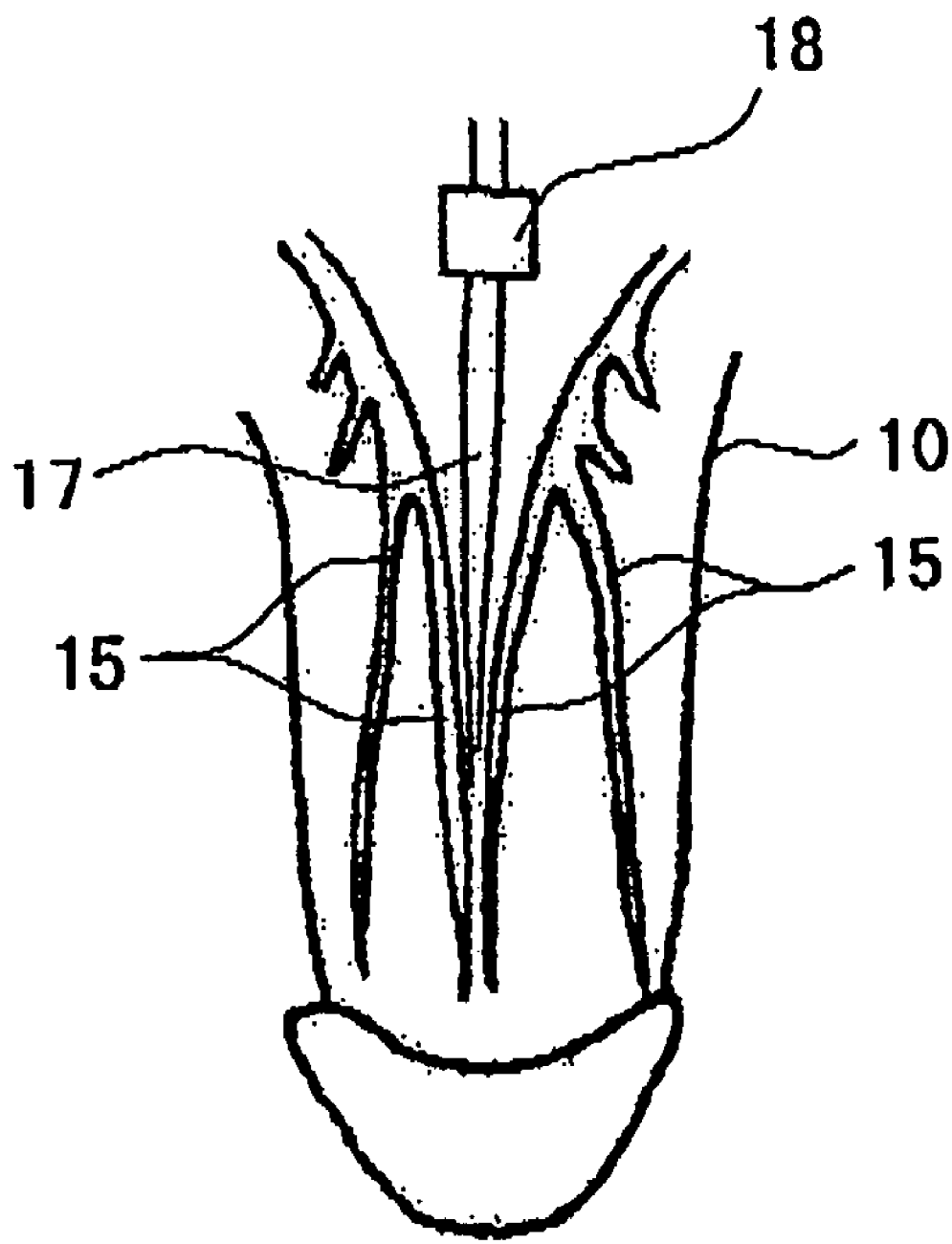
FIG. 2 is a front cross-sectional view showing the arrangement of blood vessels in the penis.

As shown in FIG. 2, two penile arteries 15 branch to the left and right in the penis 10, and the penile vein 17 runs centrally between the left and right arteries 15.

Figure 3:
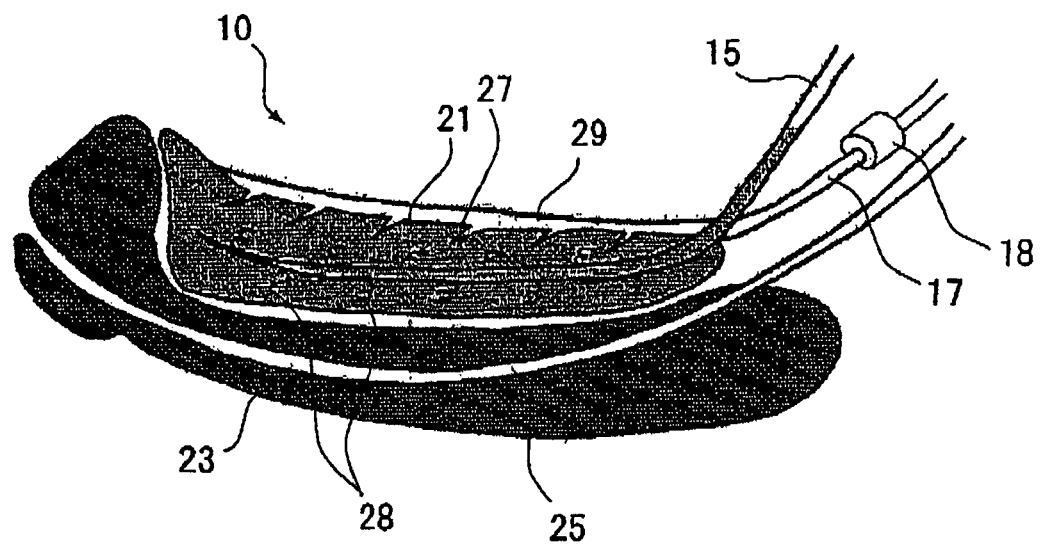
FIG. 3 is a perspective view showing the spongy body of the penis and arrangement of blood vessels.
Figure 4:
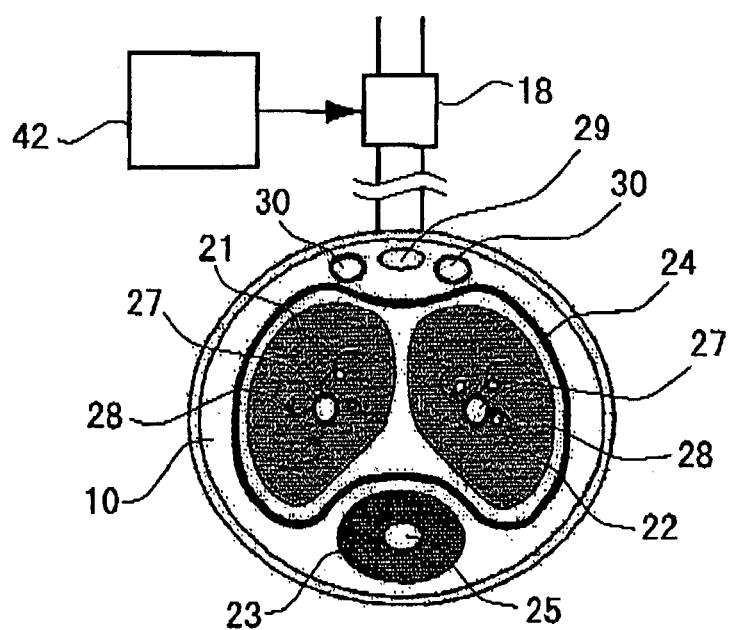
FIG. 4 is an enlarged cross-sectional view of essential parts.

FIGS. 3, 4 show the internal structure of the penis 10 with the penile artery 15 and penile vein 17 pulled out, and the structure of the spongy body. In the penis 10, there are left and right spongy bodies 21, 22 and an urethral spongy body 23 below this. These left and right spongy bodies 21, 22 are covered with a white film 24, and the spongy body 23 is situated outside the white film 24 underneath. The urethra 25 penetrates the central part of the spongy body 23.

The ends of the penile arteries 15 penetrate the central parts of the left and right spongy bodies 21, 22, forming deep penile arteries 27. Spiral arteries 28 extend radially from the deep penile arteries 27, blood being supplied to the spongy bodies 21, 22 by these spiral arteries 28. A penile dorsal vein 29 runs from the end of the penile vein 17 above the left and right spongy bodies 21, 22. Left and right dorsal penile arteries 30 also run on the outside of the white film 24 on both sides of the penile dorsal vein 29.

Figure 5:
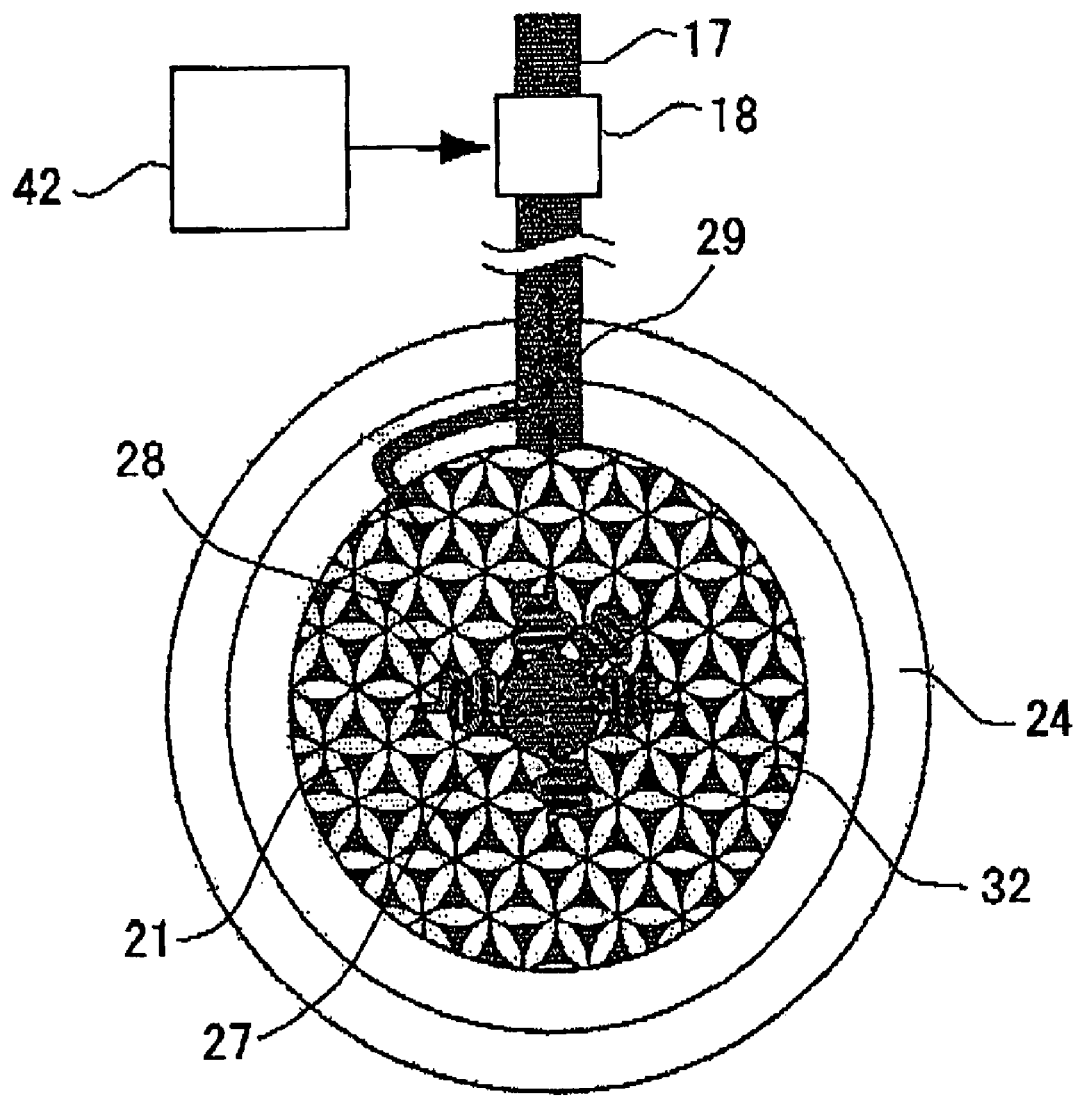
FIG. 5 is a cross-sectional view of the spongy body in the normal state.
Figure 6:
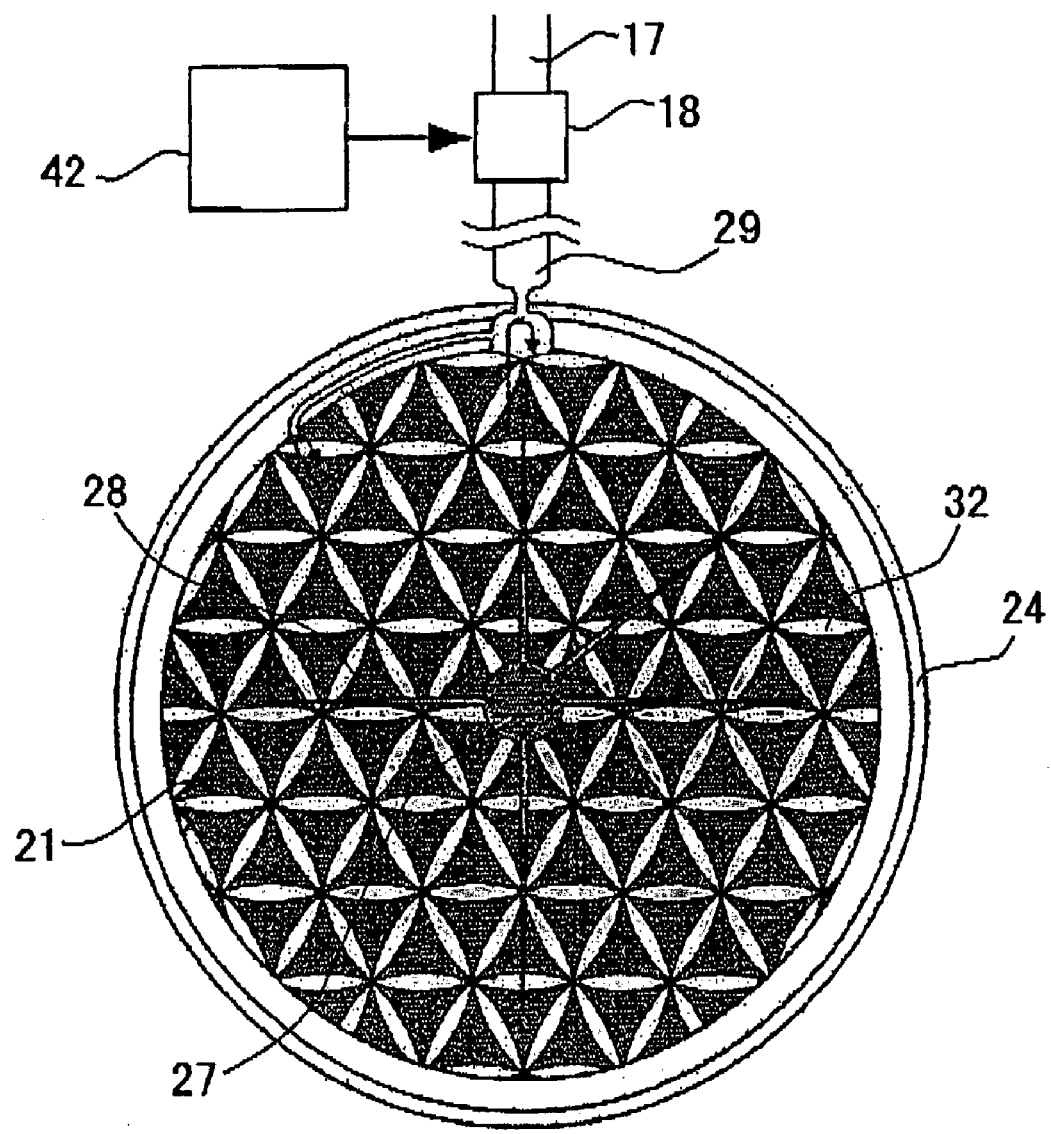
FIG. 6 is a cross-sectional view of the spongy body in the erection state.

FIGS. 5, 6 show a typical cross-sectional structure of the spongy bodies 21, 22. FIG. 5 shows the usual state, and FIG. 6 shows the erection state. In the spongy body 21 whereof the peripheral wall is covered with the white film 24, there is a meshwork of smooth muscle 32.

When the brain is excited by sexual stimulation, in the penis 10, nitric oxide acts on the smooth muscle 32 of the spongy body 21 which is in the limp state shown in FIG. 5, and the smooth muscle 32 relaxes. Blood then flows from the deep artery of the penis 27 so that the spongy body 21 is filled with blood, and the penis assumes the erection state shown in FIG. 6. Also, the spongy body 21 expands radially due to the relaxation of the smooth muscle, so the penile dorsal vein 29 connected to the peripheral wall of the spongy body 21 is constricted by the spongy body 21 and white film 24, and venous flow from the spongy body 21 is shut off. Therefore, the spongy body 21 remains expanded, and the erection state is maintained.

In the above erection state, when the stimulus from the brain stops or ejaculation occurs, a splitting enzyme phosphodiesterase (PDE) becomes active, the smooth muscle 32 contracts and the spongy body 21 shrinks. The penis 10 therefore changes from the state shown in FIG. 6 to the state shown in FIG. 5, and the constriction of the dorsal penile arteries 30 which had been gripped by the white film 24 and spongy body 21 is released. The blood in the spongy body 21 is therefore discharged to the penile vein 17 via the penile dorsal vein 29 from the spongy body 21, and the erection state is released.

In this, embodiment of the present invention, the penile dorsal vein 29 or penile vein 17 is cut at a predetermined position, the electromagnetic valve 18 is connected thereto, and the erection state is controlled by opening or closing this electromagnetic valve 18 by means of a control unit 42 implanted in the abdomen in the vicinity of the valve 18.

Figure 7:
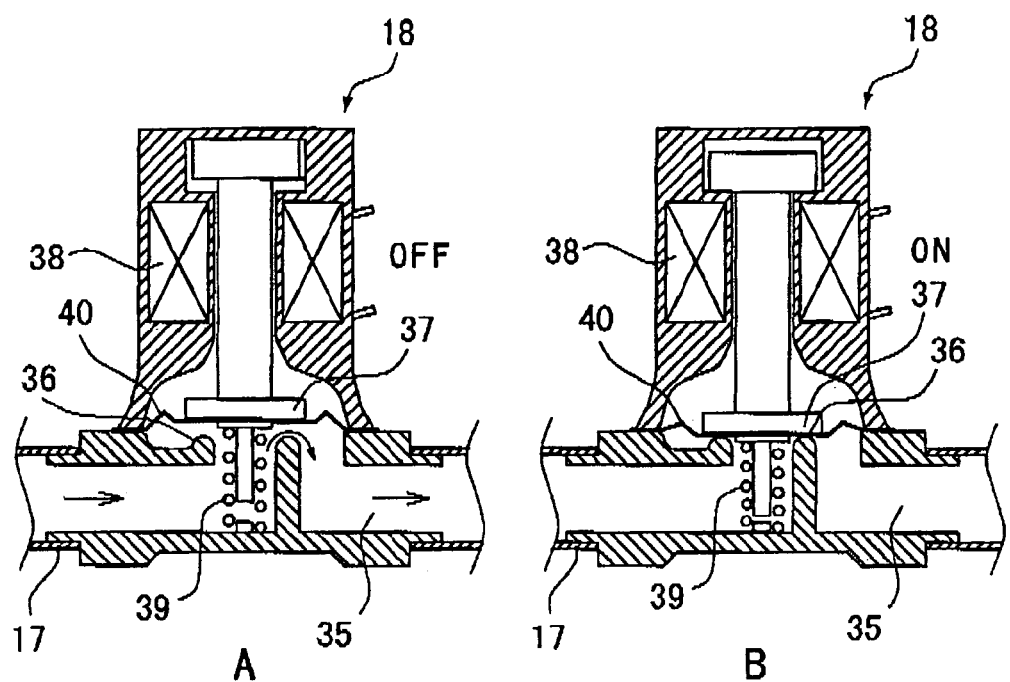
FIG. 7 is a cross-sectional view showing the internal construction of an electromagnetic valve.

In the electromagnetic valve, as shown in FIG. 7, a valve seat 36 is formed in a blood passage 35 connected to the penile vein 17, and a valve body 37 comprising a diaphragm 40 is arranged so that it can come into contact with or separate from this valve seat 36. Opening and closing control is then performed according to the balance between the magnetism of a coil 38 and the force of a spring 39. When the electric current is stopped, the electromagnetic valve 18 shown in FIG. 7 closes, but conversely it may be made to open when the coil is magnetized and close when it is demagnetized. The former method is preferred from the viewpoint of power-saving. The diaphragm 40 prevents blood from flowing into the coil 38.

The electromagnetic valve 18 may be a throttle valve which permits a small blood flow in the magnetized state. In general, in the natural erection state, the penile dorsal vein 29 is not completely constricted, but still permits a very small blood flow. Therefore in order to approximate the natural state, the electromagnetic valve 18 is a throttle valve which permits a slight blood flow even in the closed state, and thus prevents oxygen shortage of the spongy bodies 21, 22.

Figure 8:
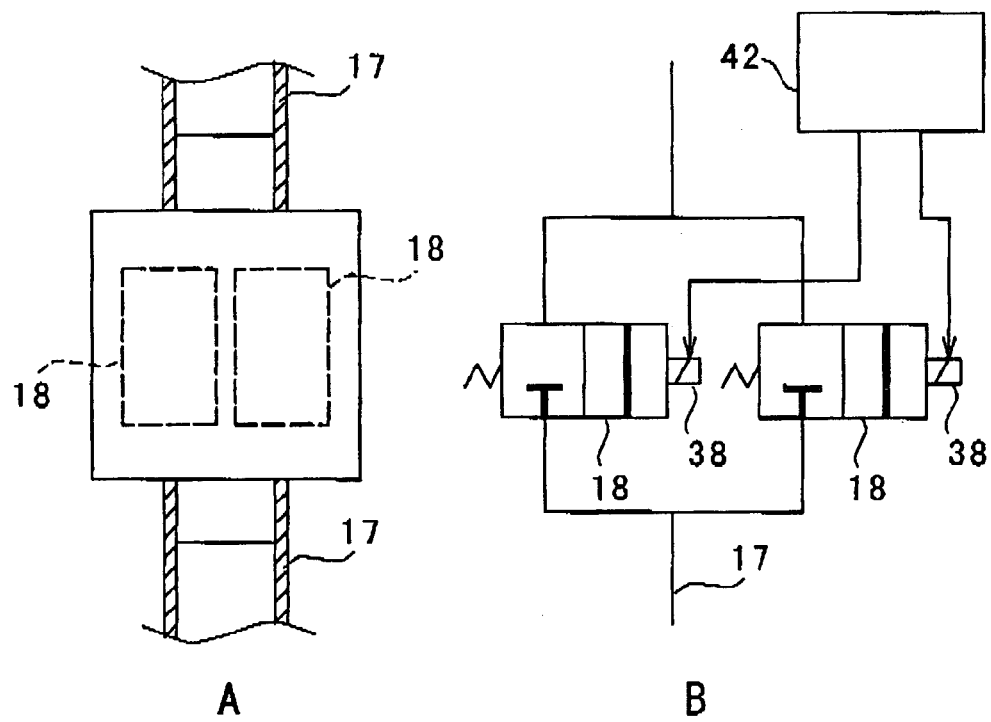
FIG. 8 is a layout diagram and circuit diagram showing connection of the electromagnetic valve according to a modification.

The electromagnetic valve 18 is not necessarily single, and as shown in FIG. 8, may instead comprise a pair of electromagnetic valves 18 connected in parallel. In this case, for example, even if one of the electromagnetic valves 18 breaks down and closes, blood flow can still be maintained by performing opening/closing control of the other electromagnetic valve 18. According to such a construction, necrosis of the penis 10 due to an oxygen shortage resulting from failure of the electromagnetic valve 18 is prevented.

Figure 9:
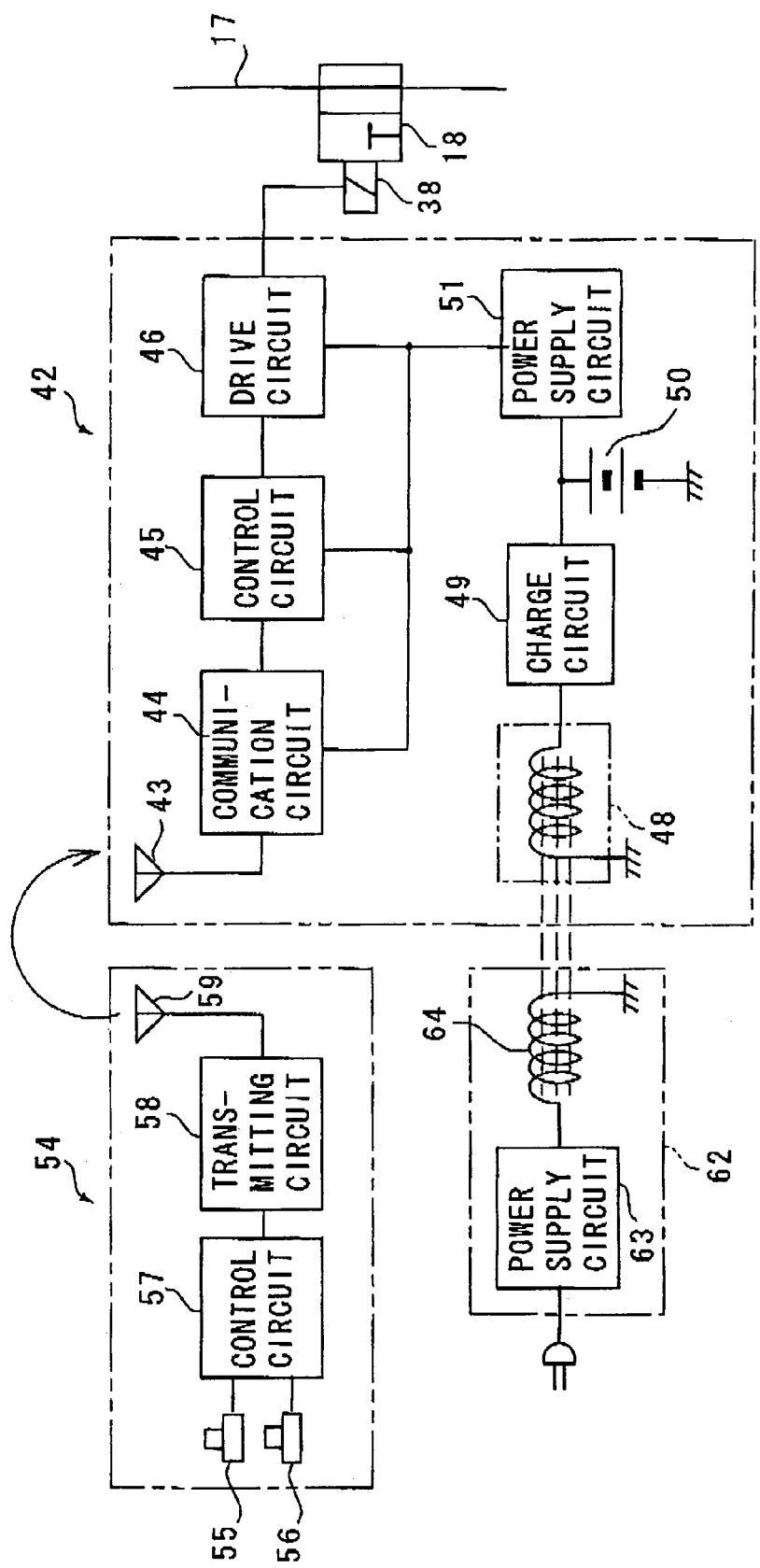
FIG. 9 is a block diagram showing the circuit construction of a control unit, commander and charger.

FIG. 9 shows the control unit 42 for opening/closing the electromagnetic valve 18, a commander 54 and a charger 62.

Here, the control unit 42 comprises a communication circuit 44 provided with an antenna 43, a control circuit 45 and a drive circuit 46. The output terminal of the drive circuit 46 is connected to the coil 38 of the electromagnetic valve 18. The control unit 42 further comprises a coil 48, charge circuit 49, secondary cell 50 and power supply circuit 51, and drives the communication circuit 44, control circuit 45 and drive circuit 46 via a power supply circuit 51.

The commander 54 comprises a pair of key switches 55, 56, control circuit 57 and transmitting circuit 58, and an antenna 59 is further connected to the output terminal of the transmitting circuit 58. Although not shown in the diagram, the commander 54 may use for example a dry cell as a power supply.

The charger 62 comprises a power supply circuit 63 which can incorporate a commercial power supply, and a coil 64 into which primary electric current flows due to the output of this power supply circuit 63.

Next, the method of controlling the erection of the penis 10 and action of the control device according to the aforesaid construction, will be described. Shut-off of the electromagnetic valve 18 may be performed when the smooth muscle 32 contracts and the penis 10 becomes limp as shown in FIG. 5, but it may be performed also when the penis becomes erect naturally, i.e., when the smooth muscle 32 relaxes, the spongy body 21 of the penis 10 is filled with blood and the dorsal vein of the penis 29 is blocked, as shown in FIG. 6. The electromagnetic valve 18 is usually open (FIG. 7A).

When the key switch 55 of the commander 54 shown in FIG. 9 is pushed, a start signal is sent to the control circuit 57. The control circuit 57 activates the transmitting circuit 58, and a radio wave is sent to the antenna 43 of the control unit 42 by wireless by the transmitting circuit 58 via the antenna 59. Since tissues of living things are almost transparent to radio waves, the communication circuit 44 receives this radio wave via the antenna 43, and supplies a signal to the control circuit 45. The control circuit 45 therefore responds to the aforesaid signal, and activates the drive circuit 46. The drive circuit 46 magnetizes or demagnetizes coil 38 of the electromagnetic valve 18, and closes the electromagnetic valve 18.

When the electromagnetic valve 18 connected to the penile vein 17 of the penis 10 is closed, the blood in the spongy body 21 of the penis 10 is prevented from flows back to the heart 11 via the lungs. At the same time, blood continues to be supplied to the central part of the spongy body 21 via the penile arteries 15 and deep penile arteries 27 from the heart 11. Therefore, the spongy body 21 expands due to blood pressure, or the expansion state is maintained as it is.

Even if the signal based on sexual stimulation from the brain is interrupted or phosphodiesterase which is a splitting enzyme is activated, the blood in the spongy body 21 does not leave, so the penis 10 remains in its erection state. This erection state is maintained as long as the electromagnetic valve 18 remains closed. The penis 10 therefore maintains its erection state until a signal to open the electromagnetic valve 18 is sent by the commander 54.

When the key switch 56 of the commander 54 shown in FIG. 9 is pushed, the control circuit 57 sends another signal to the transmitting circuit 58. The transmitting circuit 58 then sends a radio wave which includes a cancellation signal to the antenna 43 of the control unit 42 via the antenna 59. The communication circuit 44 supplies the cancellation signal to the control circuit 45, and the drive circuit 46 changes over the coil of the electromagnetic valve 18 in response to this cancellation signal. Due to this, the electromagnetic valve 18 is opened. Blood then flows out of the penile vein 17 to the lungs, the erection state of the penis 10 is canceled, and the penis 10 returns to the normal state (FIG. 5).

Here, the control unit 42 is implanted in the abdomen in the vicinity of the electromagnetic valve 18, and its output terminal is connected to the coil 38 of the electromagnetic valve 18. On the other hand, the commander 54 is operated by hand. Therefore, erection and release of the penis 10 can be freely controlled as desired simply by selectively operating the key switches 55, 56 of the commander 54. In other words, the erection state of the penis is maintained even if the instructions based on sexual stimulation from the brain stop, or phosphodiesterase is activated.

When the splitting enzyme phosphodiesterase is activated, the smooth muscle 32 contracts as shown in FIG. 5, and since it is pulled in such a direction as to cause the spongy body 21 to contract, the penis 10 becomes slightly smaller. Sildenafil citrate (Viagra) and vardenafil chloride (Levitra) have the effect of preventing the action of the aforesaid splitting enzyme. Therefore, if these drugs are taken before performing coitus and the electromagnetic valve 18 is closed during coitus, the splitting enzymes are hardly activated at all, so the smooth muscle 32 is prevented from contracting and a nearly perfect erection state can be maintained over a long time period.

As described above, the control unit 42 is implanted in the body together with the electromagnetic valve 18 in the vicinity of the penis 10. Here, if the secondary cell 50 which drives this control unit 42 discharges, opening/closing of the electromagnetic valve 18 is no longer possible. In this case, charging is performed by the charger 62. When the charger 62 is made to approach one side of control unit 42 in the abdomen, magnetic coupling between the coil 64 of the charger 62 and the coil 48 connected to the charge circuit 49 of the control unit 42 occurs. If a primary alternating current is sent through the coil 64 via the power supply circuit 63, a secondary electric current is therefore produced in the coil 48 of the control unit 42 according to the transformer principle, and the secondary cell 50 can then be charged via the charge circuit 49 by this secondary electric current. Instead of this secondary cell 50, a compact high capacity primary cell may be used.

Figure 10:
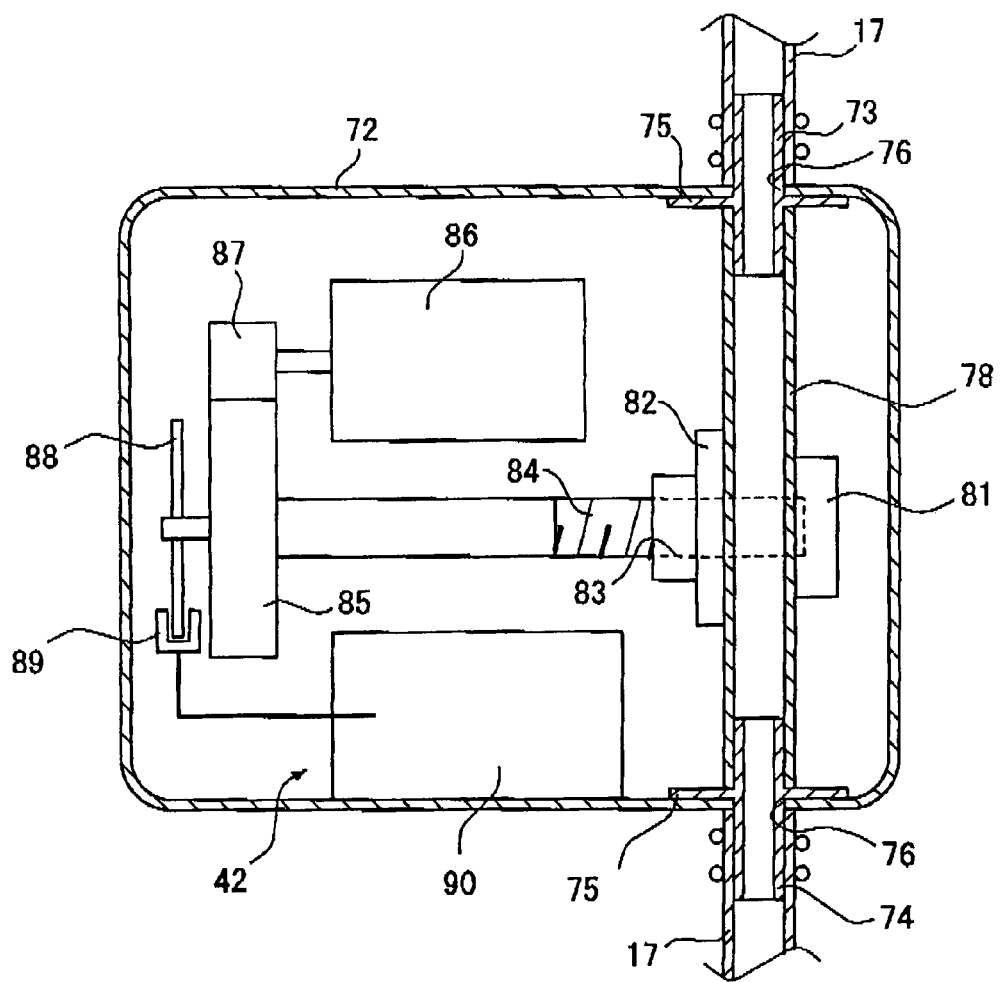
FIG. 10 is a plan view of essential parts showing an control valve according to another embodiment of the invention.

FIGS. 10-13 describe a second embodiment. According to this embodiment, as shown in FIG. 10, the housing of the ON-OFF valve and control unit 42 is an effectively rectangular casing 72, and a pair of connecting tubes 73, 74 are attached to parts of the opposite side walls of this casing 72 so that they are effectively coaxial. The connecting tubes 73, 74 are provided with flanges 75, the connecting tubes 73, 74 being attached to the casing 72 by the joining of these flanges 75 to the sides thereof on the edges of throughholes 76. A polymer tube 78 having a circular cross-section is made to pass through the connecting tubes 73, 74. The polymer tube 78 is a flexible tube having superior resilience when repeatedly bent.

Figure 11:
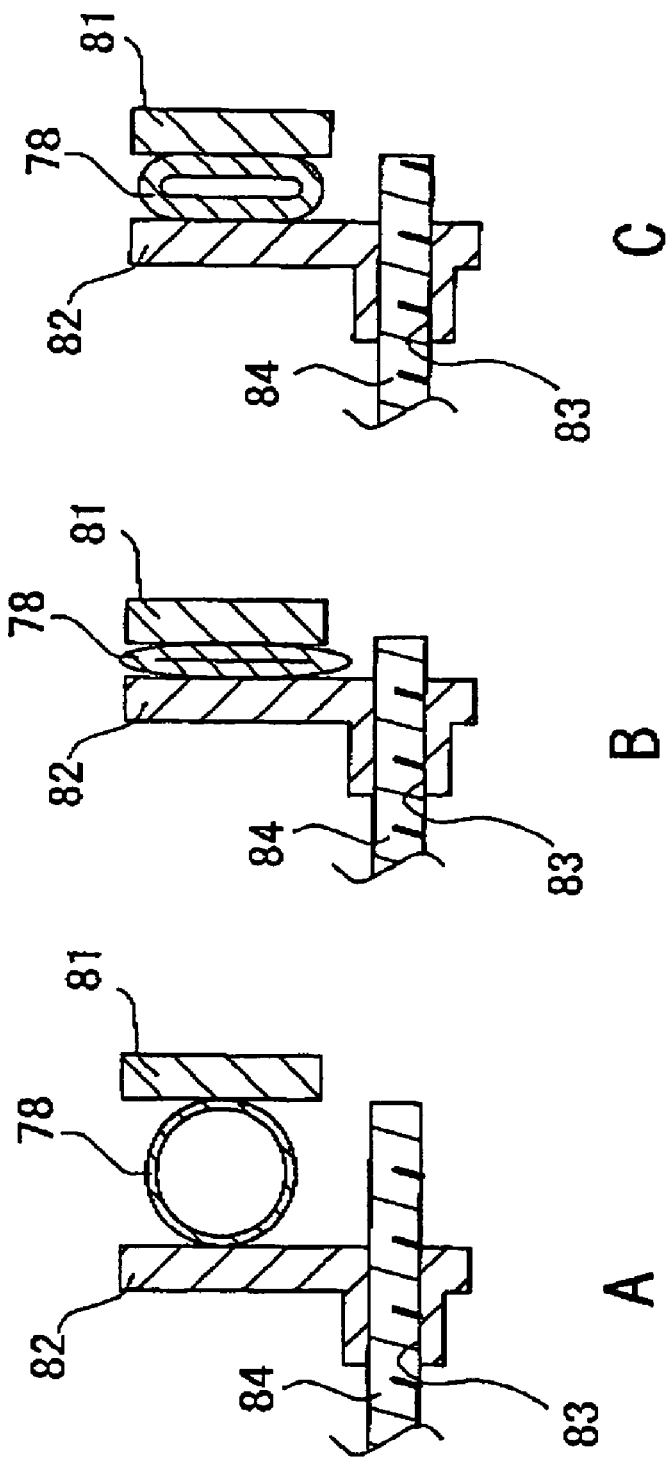
FIG. 11 is a vertical cross-section showing the opening/closing or throttling of a polymer tube by this control valve.

A backing plate 81 is fixed so as to receive one edge of the outer circumference of the polymer tube 78. A depressor 82 is arranged on the opposite side of the polymer tube 78 to the backing plate 81, this depressor 82 having a female screw hole 83 into which a feed screw 84 screws (FIG. 11). A spur wheel 85 is fixed to part of the end of the feed screw 84, this spur wheel 85 meshing with a drive gear 87 fixed to the output shaft of a motor 86. A detectable disk 88 is further attached to the spur wheel 85, the rotation of the disk 88 being detected by a detector 89. The detector 89 is connected to the control circuit 45 (FIG. 12) on a printed circuit board 90.

Figure 12:
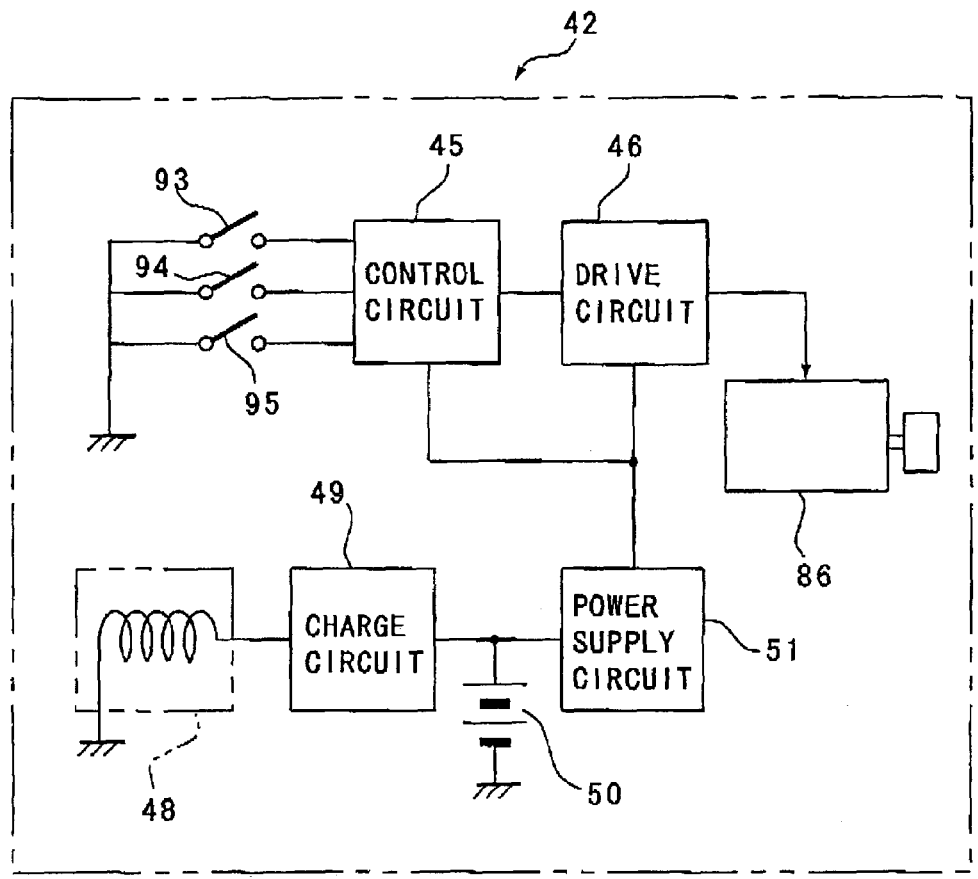
FIG. 12 is a block diagram showing the circuit construction of the control unit.

FIG. 12 describes the construction of the control circuit 45 in the aforesaid printed circuit board 90. According to this embodiment, the control unit 42 is directly controlled by switches 93, 94, 95 without using the commander 54 of the aforesaid embodiment. The switches 93, 94, 95 are connected to the input side of the control circuit 45 connected to the drive circuit 46 which drives the motor 86.

When the switch 93 is pushed, the control circuit 45 emits a signal which closes the polymer tube 78. On the other hand, when the switch 94 is pushed, the control circuit 45 emits a signal which releases the compression of the polymer tube 78 and restores this polymer tube 78 to a circular state. The switch 95 emits a signal which controls the throttling amount of the tube 78, the throttling amount of the polymer tube 78 being adjusted according to the pushing time of this switch 95. The power supply circuit of the aforesaid drive circuit 46 and control circuit 45 is identical to that of the aforesaid first embodiment, charging of the secondary cell 50 being performed by charge due to magnetic coupling.

Figure 13:
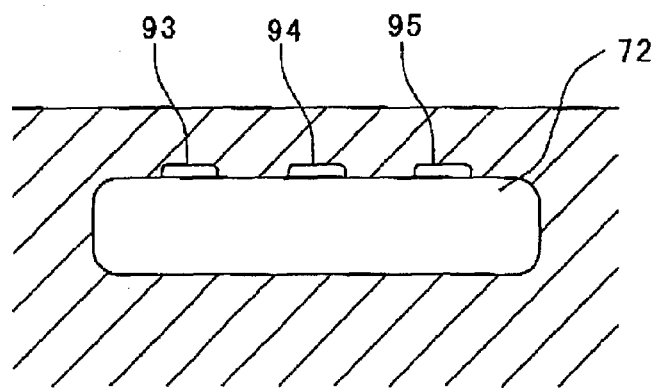
FIG. 13 is a cross-sectional view showing a state where the casing of the control unit is implanted in the body.

This control unit 42 is embedded in the skin of the abdomen inside the casing 72 shown in FIG. 13. The above three switches 93, 94, 95 can be pushed through the skin by a finger.

In the above construction, the polymer tube 78 is usually disposed between the backing plate 81 and the depressor 82 so that its cross-section is effectively circular, as shown in FIG. 11A. When the switch 93 connected to the control circuit 45 is pushed, the control circuit 45 sends a control signal to the drive circuit 46. The drive circuit 46 drives the motor 86, and the drive gear 87 drives the spur wheel 85. The feed screw 84 therefore rotates, and the depressor 82 which is screwed with this feed screw 84 is displaced towards the right, as shown in FIG. 11B. The polymer tube 78 is thereby pressed against the backing plate 81, which effectively squeezes the polymer tube 78 so as to close it. Since the ends of the polymer tube 78 are connected to the penile vein 17 via the connecting tubes 73, 74, flow of venous blood via the penile vein 17 is prevented, and as a result, the penis becomes erect.

When the switch 94 of the control unit 42 is pushed by a finger through the skin, the control circuit 45 emits a control signal to the drive circuit 46, and the motor 86 reverses. The rotation of the motor 86 is transmitted to the feed screw 84 via the drive gear 87 and spur wheel 85. Hence, the depressor 82 is pulled back by the feed screw 84, and the depressor 82 changes from the state shown in FIG. 11B to the state shown in FIG. 11A. This releases the compression of the polymer tube 78 by the depressor 82, opens the polymer tube 78 and allows venous blood to flow. The erection state of the penis is therefore released.

When the switch 95 connected to the control circuit 45 of this control unit 42 is pushed, the control circuit 45 emits a signal depending on the closing time of this switch 95, so the squeezing amount of the polymer tube 78 by the motor 86 and depressor 82 can be adjusted. If the squeezing amount of the polymer tube 78 is set to an intermediate value as shown in FIG. 11C, a small amount of blood will still flow through this polymer tube 78. The stiffness of the penis when erect can therefore be adjusted, and necrosis due to oxygen shortage of the penis can be eliminated.

Instead of adjusting the feed amount of the depressor 82 by the detectable disk 88 and detector 89 shown in FIG. 10, a gap sensor which detects the gap between the backing plate 81 and depressor 82 may be provided, and be performed feedback control of the detection output of this gap sensor performed by the control circuit 45. The throttling amount of the polymer tube 78 shown in FIG. 11C can then be feedback-controlled which permits more precise throttling control of the polymer tube 78.

Figure 14:
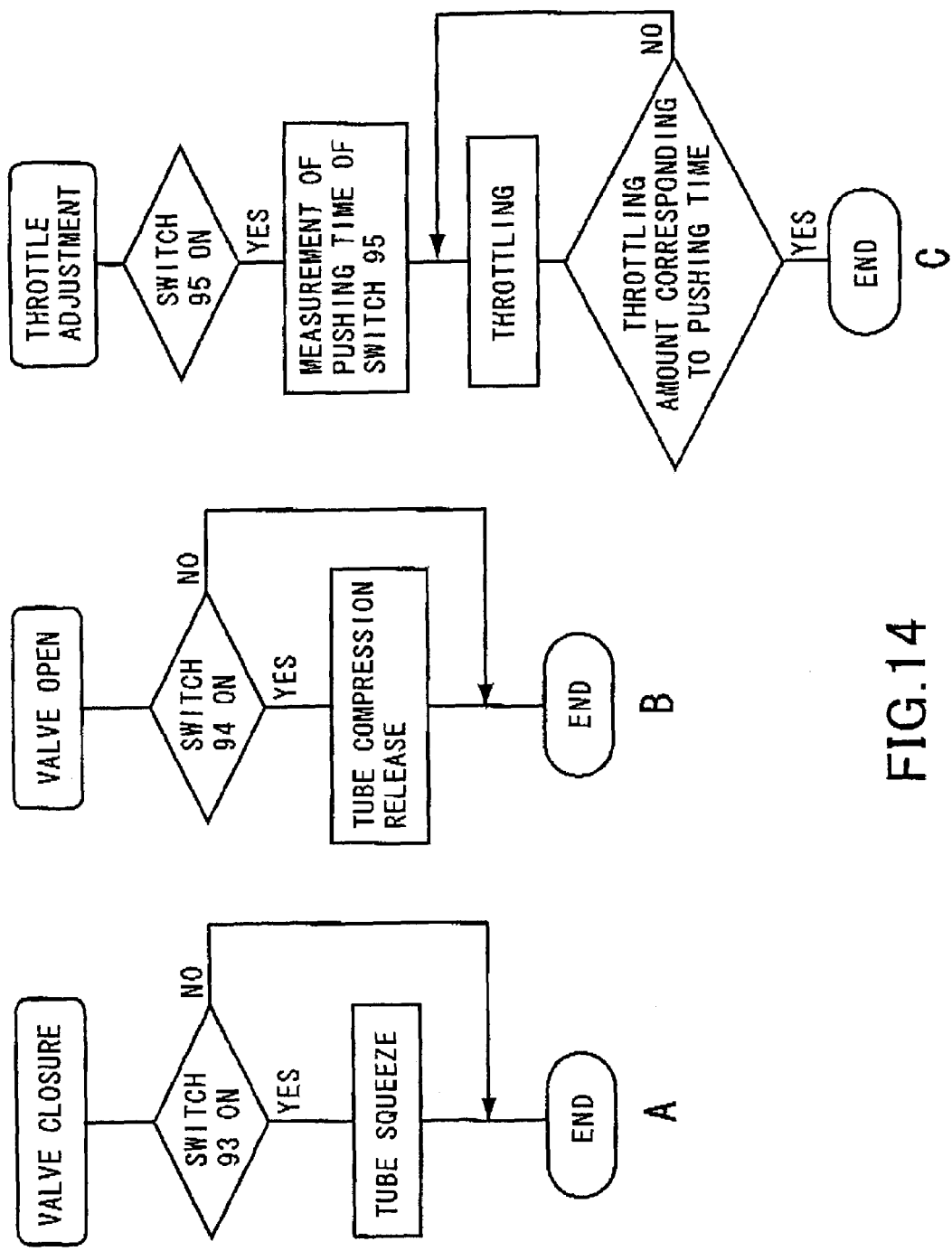
FIG. 14 is a flowchart showing the control performed when a microcomputer is provided in the control circuit of the control unit.

A microcomputer may be used for the control circuit 45 of the control unit 42. In this case, when the switch 93 is pushed, as shown in FIG. 14A, the ON state of this switch 93 can be detected and control performed so as to squeeze the polymer tube 78. When the switch 94 is pushed, as shown in FIG. 14B, the compression of the polymer tube 78 is released in response thereto. When the switch 95 is pushed, as shown in FIG. 14C, the pushing time is measured and throttling is performed according to this time measurement. When the throttling reaches a throttling amount corresponding to the pushing time, throttling stops.

Figure 15:
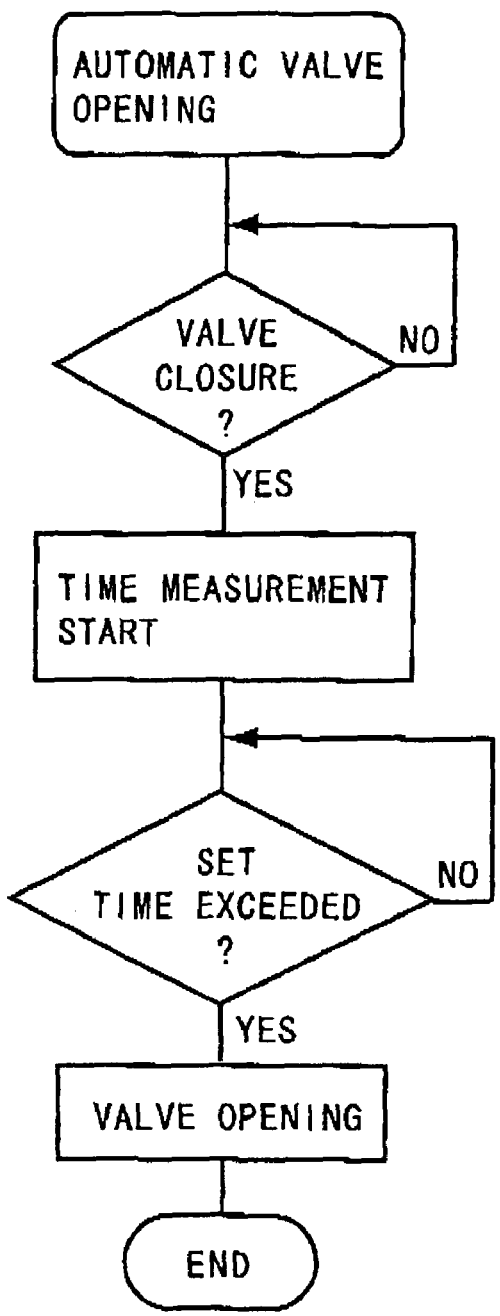
FIG. 15 is a flowchart showing an automatic valve opening action.

Next, an automatic valve opening action by a microcomputer in the control circuit 45 will be described referring to FIG. 15. This action prevents the penis from lapsing into oxygen shortage when the polymer tube 78 connected to the penile vein 17 is closed for a long time. The microcomputer determines whether or not the valve is in a closed state, and when it is detected that it is in the closed state, time measurement is started. It is then determined whether or not a predetermined time set beforehand, for example 1 hour, was exceeded, and when it is exceeded, a valve opening action is performed. Necrosis of the penis due to oxygen shortage can therefore be forestalled.

In the embodiments shown in FIGS. 10-13, a pair of ON-OFF valves comprising the polymer tube 78 and depressor 82 may be provided, these ON-OFF valves being connected in parallel with each other. In such a construction, if one ON-OFF valve breaks down and closes, blood flow can be ensured by the other ON-OFF valve, and safety can be enhanced in the event of a failure.

The invention has been described referring to the embodiments shown in the diagrams, but the invention is not limited to the aforesaid embodiments, various modifications being possible within the scope and spirit of the appended claims. For example, the electromagnetic valve 18 of the first embodiment can be transposed to the polymer tube 78 of the second embodiment. In the second embodiment, the coil 38 of the electromagnetic valve 18 may be controlled instead of the motor 86 by the drive circuit 46. Also, various modifications may be made to the electromagnetic valve 18 or circuit construction of the control unit 42 which controls the motor 86.

The present invention has wide application as a control unit to control the erection state of the penis, which is the male sex organ, and can be used to prevent penis dysfunction and age-related decline of male sexual function. It is therefore of value in restorative medical devices.

What is claimed is:

1. A penile erection control device, comprising:
   valve means adapted to be connected to a vein which returns blood from a spongy body of a penis to lungs; and
   control means connected to the valve means, said control means controlling ON-OFF control or opening adjustment of said valve means so that an erection state is maintained by using said control means to close or throttle said valve means, said control means having means to forcibly open the valve means when the valve means is maintained substantially in a closing state for a predetermined time.

2. The penile erection control device according to claim 1, wherein said valve means is an electromagnetic valve.

3. The penile erection control device according to claim 1, wherein said control valve means is an electromagnetic squeeze valve.

4. The penile erection control device according to claim 1, wherein said valve means is connected to a penile dorsal vein.

5. The penile erection control device according to claim 1, wherein said valve means has a flexible tube and a depressor which squeezes said tube so as to close or throttle said valve.

6. The penile erection control device according to claim 5, wherein said flexible tube is made of a synthetic polymer material, and both ends thereof are connected to a penile dorsal vein via a connecting tube.

7. The penile erection control device according to claim 1, wherein said control means comprises:
   a control unit adapted to be implanted in a body, which controls the opening/closing or throttling amount of said valve means; and
   a commander which sends control signal to said control unit.

8. The penile erection control device according to claim 1, wherein said control means comprises a control unit adapted to be implanted in a body which controls the ON-OFF control or opening adjustment of said valve means, and a pressure-sensitive control panel is provided on an outer surface of a casing of said control unit, a control signal being supplied to said control unit by pressing said control panel through a skin.

9. The penile erection control device according to claim 1, wherein said control means comprises measurement means which measures time, and when said measurement means measures a predetermined time from when said valve means is closed or throttled, opens said valve means, said measurement means forming said means to forcibly opening the valve means.

10. A penile erection control method comprising:
    closing valve means connected to a vein returning blood from a spongy body of a penis to lungs through control means to enlarge the penis, and
    forcibly opening said valve means through the control means when said valve means is maintained in a closing state for a predetermined time.

11. The penile erection control method according to claim 10, wherein said closing the valve means includes adjustment of an opening of the valve means to control blood flow in the vein.

12. The penile erection control method according to claim 10, wherein said control means controls an electromagnetic valve of the valve means.

13. The penile erection control method according to claim 10, wherein said control means controls an electromagnetic squeeze valve of the valve means.

14. The penile erection control method according to claim 10, wherein the valve means controls a blood flow in a penile dorsal vein to which said valve means is connected.

* * * * *